US00PP34048P2

(12) United States Plant Patent
Dofferhoff

(10) Patent No.: US PP34,048 P2
(45) Date of Patent: Mar. 22, 2022

(54) ***HYDRANGEA* PLANT NAMED 'B10'**

(50) Latin Name: *Hydrangea paniculata*
Varietal Denomination: B10

(71) Applicant: Greenwood Investments B.V., Reeuwijk (NL)

(72) Inventor: Hans Dofferhoff, Reeuwijk (NL)

(73) Assignee: GREENWOOD INVESTMENTS B.V., Reeuwijk (NL)

( * ) Notice: Subject to any disclaimer, the term of this patent is extended or adjusted under 35 U.S.C. 154(b) by 0 days.

(21) Appl. No.: 17/370,157

(22) Filed: Jul. 8, 2021

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
See application file for complete search history.

*Primary Examiner* — Susan McCormick Ewoldt
(74) *Attorney, Agent, or Firm* — Penny J. Aguirre

(57) ABSTRACT

A new cultivar of *Hydrangea paniculata* plant named 'B10' that is characterized by its broadly obovate and upright growth habit, its compact and short plant habit, its very conical inflorescences that are white in color and turn pink in autumn, and its foliage that is dark green and sturdy.

2 Drawing Sheets

Botanical classification: *Hydrangea paniculata.*
Varietal denomination: 'B10'.

BACKGROUND OF THE INVENTION

The present invention relates to a new and distinct cultivar of *Hydrangea paniculata* and will be referred to hereafter by its cultivar name, 'B10'. 'B10' represents a new panicle *Hydrangea*, a perennial shrub grown for landscape use and as a potted plant. 'B10' was discovered as a chance seedling by the Inventor in a production field of numerous proprietary seedlings of *Hydrangea paniculata* in Reeuwijk, The Netherlands in August of 2019. The parent plants are unknown.

Asexual propagation of the new cultivar was first accomplished by stem cuttings by the Inventor in September of 2019 in Reeuwijk, The Netherlands. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'B10' as a unique cultivar of *Hydrangea paniculata.*

1. 'B10' exhibits a broadly obovate and upright growth habit.
2. 'B10' exhibits a compact and short plant habit.
3. 'B10' exhibits very conical inflorescences that are white in color and turn pink in autumn.
4. 'B10' exhibits foliage that is dark green and sturdy.

'B10' can be most closely compared to the *Hydrangea paniculata* cultivars 'B2' (U.S. Plant Pat. No. 32,316) and 'ILVOBO' (U.S. Plant Pat. No. 22,782). Both are similar to 'B10' in having dwarf plant habits. 'B2' differs from 'B10' in having sterile flower sepals that are creamy white-light green in color that become slightly flushed with rose pink as they age, inflorescences that are larger in size and rounder in shape, and a shorter plant height. 'ILVOBO' differs from 'B10' in having sterile flower sepals that are brighter white-light green in color, inflorescences that are more rounded in shape, and a less compact plant habit.

BRIEF DESCRIPTION OF THE DRAWINGS

The accompanying color photographs illustrate the overall appearance and distinct characteristics of the new *Hydrangea*. The photographs were taken of a two-year-old plant of 'B10' as field grown in Reeuwijk, The Netherlands and placed in a 27-cm container for the photographs.

The photograph in FIG. 1 provides a side view of the plant habit of 'B10' in bloom.

Figure 1:
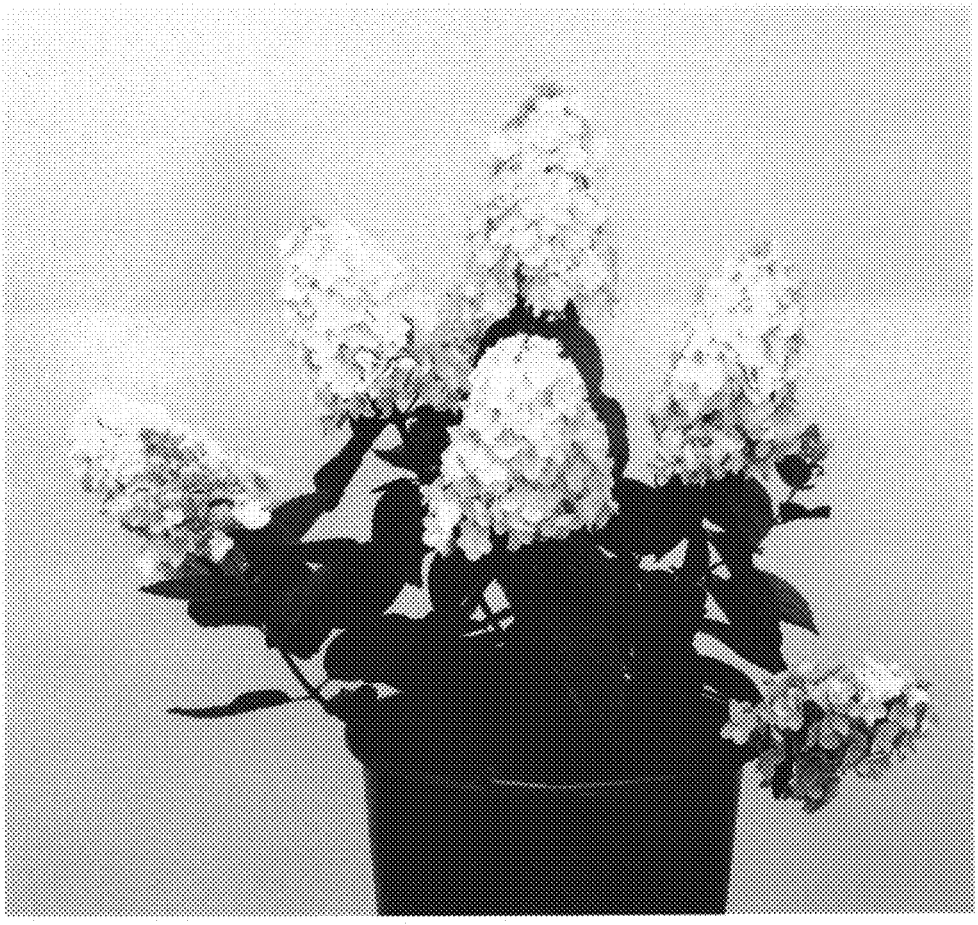
Figure 2:
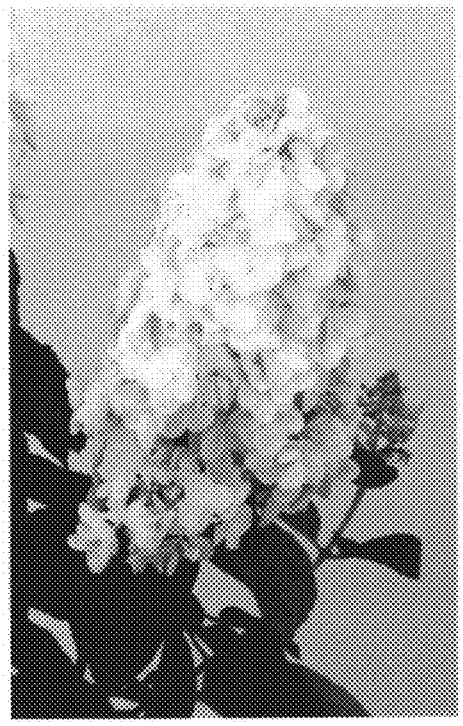

The photograph in FIG. 2 provides a close-up view of an inflorescence of 'B10'.

Figure 3:
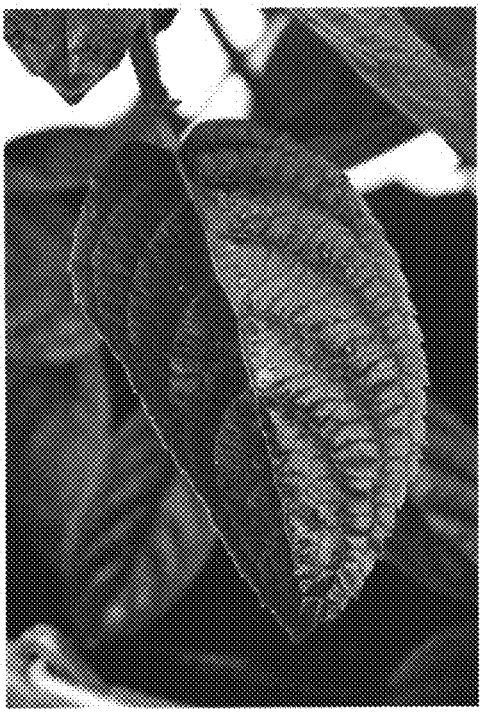

The photograph in FIG. 3 provides a close-up view of a leaf of 'B10'.

The colors in the photographs are as close as possible with the photographic and printing technology utilized and the color values cited in the detailed botanical description accurately describe the colors of the new *Hydrangea.*

BOTANICAL DESCRIPTION OF THE PLANT

The following is a detailed description of two-year-old plants of 'B10' as field grown in Reeuwijk, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—July and August in the Netherlands.
*Plant type.*—Herbaceous shrub.
*Plant habit.*—Compact and broadly obovate and upright.
*Height and spread.*—Reaches 58 cm in height, 70 cm in spread.

*Hardiness.*—At least in U.S.D.A. Zones 5 to 9.

*Diseases and pests.*—No susceptibility and resistance to diseases or pests has been observed.

*Root description.*—Fine, fibrous and dense, NN155A and 164A in color.

*Propagation.*—Stem cuttings.

*Root development.*—An average of 6 weeks for root initiation with a finished plant produced in about 12 months.

*Growth rate and vigor.*—Moderate to high.

Stem description:

*Stem shape.*—Rounded.

*Stem strength.*—Strong.

*Stem color.*—Young; 147C, mature; 197A to 197B, upper surface (sunny side) 177A to 177B, old bark; N199C and 200D.

*Stem size.*—Average of 28 cm in length (excluding inflorescence) and 6 mm in diameter.

*Stem surface.*—Young stems are matte and densely covered with stiff hairs, average of 0.5 mm in length and match surface color, mature stems are matte and moderately covered with lenticels that are an average of 1.5 mm in length and 0.75 mm in diameter, 165C in color, no fasciation of mature bark was observed.

*Stem aspect.*—Upright, average of 55° to soil level.

*Internode length.*—An average of 5.2 cm.

*Branching.*—Freely branching with an average of 9 lateral branches.

Foliage description:

*Leaf shape.*—Broadly ovate to elliptic.

*Leaf arrangement.*—Opposite or in whorls of three.

*Leaf division.*—Simple.

*Leaf base.*—Obtuse to truncate.

*Leaf apex.*—Apiculate.

*Leaf margins.*—Serrate.

*Leaf venation.*—Pinnate, color; upper surface 146C, lower surface 145B.

*Leaf size.*—An average of 11.7 cm in length and 7.9 cm in width.

*Leaf attachment.*—Petiolate.

*Leaf number.*—An average of 8 per lateral stem.

*Leaf surface.*—Both surfaces; matte and slightly rugose, upper surface sparsely covered with short hairs, an average of 0.75 mm in length, color; upper surface hairs 156D, lower surface hairs 157A.

*Leaf color.*—Young upper surface; 137A, young lower surface 147B, mature and fall upper surface; NN137A and 147A, mature lower surface; 147B.

*Petioles.*—An average of 1.5 cm in length and 3 mm in diameter, upper surface color 144B, proximal end 146A, lower surface color 146B to 146C, both surfaces matte, and sparsely covered with short hairs; an average of 0.3 mm in length, too small to measure color.

Inflorescence description:

*Inflorescence type.*—Terminal conical panicle, comprised of sterile flowers above inconspicuous fertile flowers.

*Lastingness of inflorescence.*—Sterile flowers; persistent for an average of 6 weeks, fertile flowers; self-cleaning, an average of 5 days.

*Inflorescence number.*—One per lateral stem.

*Inflorescence size.*—An average of 20.2 cm in height and 14.5 cm in diameter.

*Flower number.*—An average of 400 sterile flowers and 750 fertile flowers per panicle.

*Flower fragrance.*—Faint, sweet and pleasant.

*Flower aspect.*—Sterile flowers; held upright to outward and slightly drooping, fertile flowers; held upright from peduncle.

*Flower size.*—Sterile flowers; up to 3.6 cm in diameter and 1.2 cm in depth, fertile flowers; an average of 6 mm in diameter and 5 mm in depth.

*Flower type.*—Sterile flowers rotate, fertile flowers rotate, dropped when mature.

*Flower buds.*—Sterile flowers; an average of 8 mm in length and 1.2 cm in diameter, broadly cup-shaped, 150C to 150D in color, fertile flowers; an average of 3 mm in length, 2 mm in diameter, obovate in shape, color; 145D, immature calyx 145B.

*Petals.*—Sterile flowers; 5, ovate to concave in shape, acute apex, entire margins, cuneate base, up to 3 mm in length and 1.5 mm in width, both surfaces; glabrous and matte, color when opening and fully open upper and lower surface; NN155D, fertile flowers; 5, rotate and cruciform in shape, ovate to concave in shape, acute apex, cuneate base, entire margins, average of 3 mm in length and 1.5 mm in width, both surfaces glabrous and matte, color; upper surface when opening and fully open 155A, lower surface when opening and fully open NN155D, petals drop at maturity.

*Peduncles.*—Primary peduncles; strong, flattened oval in shape, an average of 3 cm in length and 2 mm in width and 165C in color, secondary peduncles 2 cm in length and 2 mm in width, 157D in color, surfaces are matte and moderately covered with thin pubescence an average of 0.4 mm in length and 145D in color.

*Pedicels.*—Sterile flowers; moderate strength, an average of 1.4 cm in length and 1 mm in width, 157D in color, held at a 45° angle, 145D in color, surface is matte and moderately covered with thin pubescence an average of 0.3 mm in length and 157D in color, fertile flowers; moderate strength, an average of 2 mm in length, 0.5 mm in diameter, held at a 40° angle, 145D in color, surface is matte and densely covered with thin pubescence an average of 0.4 mm in length and 145D in color.

*Sepals.*—Sterile flowers; 4 (occasionally 5), rotate, broad ovate to slightly concave in shape, highly overlapping, obtuse to slightly emarginate apex, rounded to truncate base, entire margins, up to 1.8 cm in length and 1.6 cm in width, both surfaces; glabrous and matte, color; upper and lower surface when opening; between 155A and 157C, upper and lower surface when fully open; 155A, both surfaces fading to 145A, and become strongly tinged with 180B, fertile flowers; 5, rotate, broadly deltoid in shape, broad acuminate apex, broad cuneate base, entire margins, 1 mm in length, 1.5 mm in width, both surfaces glabrous and matte, upper and lower surface when opening and fully open 145C in color.

*Bracts.*—Sterile flowers; 1 present on each pedicel, elliptic in shape, acute apex, cuneate base, entire margins, 7 mm in length, 5 mm in width, upper surface color 144C, lower surface color 145C, fertile flowers; none.

Reproductive organs:

*Gynoecium.*—Sterile flowers; 1, occasionally 2 pistils, an average of 1 mm in length, stigma; club-shaped and 157A in color, style; 0.5 mm in length, 150D in color, ovary is 154D in color, fertile flowers; 3 pistils, an average of 1.5 mm in length, stigma; club-shaped and 157D in color, style; 0.5 mm in length, 146D in color, ovary is 147D in color.

*Androecium.*—Sterile flowers; stamens; average of 10, filaments; 2 mm in length and 155A in color, anthers; broad oblong in shape, 0.5 mm in length, 155D in color, pollen; moderate in quantity, 158D in color, fertile flowers; stamens; average of 10, filaments; 3 mm in length, 155A in color, anthers; broad oblong in shape, 0.5 mm in length, 155D in color, pollen; moderate quantity, 158D in color.

*Fruit and seed.*—None observed to date.

It is claimed:

1. A new and distinct cultivar of *Hydrangea* plant named 'B10' substantially as herein illustrated and described.

* * * * *